United States Patent [19]

Latsch et al.

[11] 4,372,270

[45] Feb. 8, 1983

[54] METHOD AND APPARATUS FOR CONTROLLING THE COMPOSITION OF THE COMBUSTIBLE MIXTURE OF AN ENGINE

[75] Inventors: Reinhard Latsch, Vaihingen; Valerio Bianchi, Hochdorf, both of Fed. Rep. of Germany

[73] Assignee: Robert Bosch GmbH, Stuttgart, Fed. Rep. of Germany

[21] Appl. No.: 747,676

[22] Filed: Dec. 6, 1976

[30] Foreign Application Priority Data

Dec. 6, 1975 [DE] Fed. Rep. of Germany ....... 2554988

[51] Int. Cl.³ .............................................. F02B 3/00
[52] U.S. Cl. .................................... 123/440; 123/489
[58] Field of Search ................................. 60/288, 276; 123/119 EC, 440, 489, 32 EA, 32 EE

[56] References Cited

U.S. PATENT DOCUMENTS

| | | | |
|---|---|---|---|
| 3,744,461 | 7/1973 | Derek | 123/32 EE |
| 3,841,283 | 10/1974 | Wood | 123/119 EC |
| 3,874,171 | 4/1975 | Schmidt et al. | 123/32 EE |
| 3,903,853 | 9/1975 | Kizler et al. | 123/32 EE |
| 3,908,366 | 9/1975 | Masaki | 60/277 |

*Primary Examiner*—Ronald B. Cox
*Attorney, Agent, or Firm*—Edwin E. Greigg

[57] ABSTRACT

An internal combustion engine is provided with an ion current sensor in the exhaust conduit. The sensor may be simply a spark plug across which is applied the vehicle battery voltage. The operation of the engine at various values of mixture composition yields characteristic curves for the ion current and for the fluctuations in the ion current as a function of the air number. These characteristic data are used to provide set point values against which the prevailing ion current is compared. If a set point value is exceeded, the fuel-air mixture is adjusted accordingly by an integral controller.

24 Claims, 6 Drawing Figures

4,372,270

METHOD AND APPARATUS FOR CONTROLLING THE COMPOSITION OF THE COMBUSTIBLE MIXTURE OF AN ENGINE

BACKGROUND OF THE INVENTION

The invention relates to a method and an apparatus for determining the composition of the mixture fed to an internal combustion engine by sensing the magnitude of operational engine parameters.

Several methods are known for regulating the composition of a fuel-air mixture in an internal combustion engine so as to obtain exhaust gases as free from toxic components as possible. For example, the engine may be regulated to operate with a stoichiometric mixture having an air number $\lambda = 1$.

For this purpose, operational parameters of the engine are sensed, for example the exhaust gas composition, with the aid of an oxygen sensor which measures the presence of free oxygen in the exhaust gas of the engine. Such known oxygen sensors have the advantage of generating a clear and regular control signal during the transition from a hyper-stoichiometric to a hypo-stoichiometric mixture and vice versa when the air number $\lambda$ traverses the value 1.0 but they have the disadvantage of being fairly expensive since they have a platinum containing surface material and their life time is relatively short because of thermal and mechanical loads.

OBJECT AND SUMMARY OF THE INVENTION

It is therefore a principal object of the invention to provide a method using a transducer which senses an operational engine parameter which is a measure of the exhaust gas composition of the engine. The transducer must deliver a clearly defined and steady control signal and be of relatively simple construction as well as being capable of withstanding the relatively rough conditions in an internal combustion engine.

It is a further object of the invention to provide an apparatus for applying this method to the control of the exhaust gas composition of an engine. The method and apparatus are intended to maintain a flawless operation of the engine, to obtain exhaust gases as free from toxic components as possible while at the same time avoiding the above-mentioned disadvantages.

These and other objects are attained according to the invention by providing a per se known ion current detector located downstream of the exhaust valves in the exhaust gas system of the engine which measures the magnitude of post combustive reactions in the gas leaving the combustion chambers of the engine. An electronic regulator or processor then uses the information in the ion current from the ion current sensor to provide appropriate control signals for changing the composition of the fuel-air mixture admitted to the engine.

In an application of the above method, the ion current is a controlled variable which is compared with a command variable within a controller and, depending on the deviation from the command value or nominal value, the controller sets a final control element which changes the composition of the operational mixture and/or of the exhaust gas of the engine. The apparatus for attaining the desired objects and for performing the method of the invention provides at least one ion current detector in the exhaust gas of the engine and a comparison circuit followed by an integral controller which influences a final control element which changes the composition of the fuel-air mixture and/or the exhaust gases.

By using the method and apparatus of the invention, the fuel-air mixture fed to the engine may be altered with respect to its components, i.e., fuel, oxidizer, especially air, and possibly recycled exhaust gas, in the desired proportions so as to obtain the most desirable exhaust gas characteristics. The exhaust gas composition may also be changed in independent manner by changing the ignition timing.

The invention will be better understood as well as further objects and advantages thereof become more apparent from the ensuing detailed description of an exemplary embodiment of the invention and several embodiments of processing circuitry for the ion current sensor signal.

DESCRIPTION OF THE PREFERRED EMBODIMENTS

A. Introduction

The various steps of the method and the elements of the apparatus for carrying out this method and for maintaining optimum operation of the engine will now be described. It is known that, when the operational mixture of an engine is hypo-stoichiometric, corresponding to air numbers $\lambda < 1$, not all the oxygen is actually used in the cylinder of the engine and a small percentage of free oxygen is still present in the exhaust gases expelled from the cylinders. It is further known that when the mixture supplied to an externally ignited engine is increasingly leaned out, the combustion process is displaced to a greater extent into the domain of the expansion stroke of the piston until, finally, there takes place a well-defined post combustion process within the exhaust system of the engine. This fact may be ascribed to the increasing portion of uncombusted oxygen in the exhaust gas when the mixture is excessively leaned out. The magnitude of this post combustive reaction may be detected by means of an ion current sensor, located as shown in FIG. 2 downstream of the exhaust valves within the exhaust system of the engine.

B. Preferred Embodiments

Figure 2:
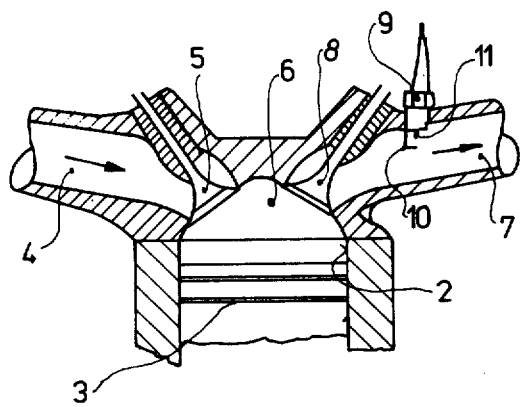
FIG. 2 illustrates the disposition of an ion current sensor in the exhaust system.

Turning now to FIG. 2, there is shown in simplified form a portion of a cylinder 2 of an internal combustion engine. Moving within the cylinder 2, in the customary reciprocating manner, is a piston 3. During its first downward stroke, the piston aspirates the fuel-air mixture through an induction tube 4 and an open inlet valve 5 into the combustion chamber 6. In known manner, an exhaust gas conduit 7 leads from the combustion chamber to an exhaust system, not further shown. An outlet valve 8 controls the communication between the combustion chamber 6 and the exhaust conduit 7 in known manner. As a major feature of the invention, there is disposed within the exhaust line 7 and downstream of the exhaust valve 8 an ion current sensor 9. In the present example, this sensor is a commercial spark plug with an insulated electrode 11 cooperating with a ground electrode 10 or even with the grounded walls of the exhaust manifold 7.

If a potential is applied across the electrodes 10 and 11, an ion current will flow as soon as an ionization of the gases between the electrodes occurs due to a post-combustion process. A relatively low voltage suffices to obtain an ion current, for example the normal battery voltage of the vehicle in which the engine is operating. The normal high voltage insulation exhibited by commercial spark plugs would not be necessary in principle; a simple insulated electrode mounted within the exhaust line 7 would be sufficient. In particular, a ground electrode such as illustrated in FIG. 2 is not necessary because the entire wall of the exhaust system serves as a ground electrode. If the ion-receiving surface of the electrode is enlarged and/or the potential is increased, the ion current increases for a constant degree of ionization of the surrounding gas.

Figure 1:
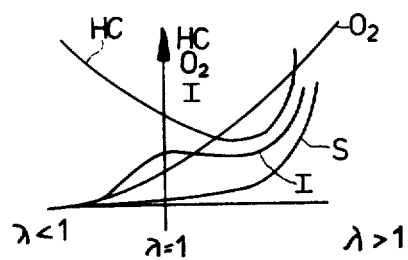
FIG. 1 is a diagram showing the integrated ion current I at the outlet of the cylinder as a function of the air number during one operational cycle of an engine piston.

FIG. 1 is a diagram illustrating the behavior of several components of the exhaust gas as a function of the air number $\lambda$. In particular, the diagram illustrates the magnitude of uncombusted hydrocarbons (HC), and residual oxygen ($O_2$); the hydrocarbon curve exhibits a minimum in the regin of air numbers around $\lambda > 1.0$ and this minimum indicates the region of the minimum fuel consumption of an engine. The curve labeled I is the ion current flowing through an ion sensor of the type described above. This curve I has a rapid rise in he domain of $\mu > 1$ and continues with a smaller slope and finally experiences another steep rise in the vicinity of the minimun of the curve HC. The first portion of this curve is determined by the post reaction of the oxygen which begins to rise in this region. The latter part of the reaction is determined by the rapid increase of the HC curve. In this region, the exhaust gas contains sufficient combustible components which then react with the ample amount of oxygen present. Both of the steep increases of the ion current curve may be used, according to the invention, for controlling the fuel-air mixture admitted to an internal combustion engine. For this purpose, optimum operational points on the curves are chosen lying in a rich region, i.e., when the engine is to deliver high torque, or in a lean region for a more economical operation of the engine.

The illustrated curve I is the result of integrated ion currents during one operational cycle of the engine. It is necessary to integrate the current over one cycle because the maximum of the post-combustion process occurs at very different times and, during a single cycle, very prominent changes in the reaction and hence of the ion currents take place. The curve S also shown in the diagram of FIG. 1 illustrates the fluctuations of sequential integrated ion currents per cycle. This curve also exhibits a well-defined increase in the region of the HC minimum at air number $\lambda > 1$, i.e., at the lean running limit of the internal combustion engine. This increase in the curve S may also be used for controlling the fuel-air mixture as may the relative fluctuations of the integrated ion currents $\Delta I/|I|$, i.e., the fluctuations with respect to the instantaneous value of the measured ion current.

The first increase of the characteristic curve I in the full-load domain of the engine, i.e., when $\lambda < 1$ and corresponding to a rich mixture, becomes more pronounced the closer the ion current sensor is physically located to the exhaust orifice of the exhaust gases from the combustion chamber 6 near the valve 8. This fact may also be caused by the turbulent admixture of the exhaust gases directly behind the outlet valve which favors the homogenization of uncombusted fuel and oxygen. The outlet valve itself acts as a flame supporter. The foregoing remarks illustrate that an ion current sensor may be used to define characteristic operating points of the engine both in the lean operating region as well as in the full-load domain if the ion currents are supplied to a controller which adjusts the mixture accordingly. It has been found that when the exhaust gas recycle rate is increased and if the ignition timing $\alpha_z$ is changed in the direction of the top dead center, there occurs a well-defined increase of the ion current and of its fluctuations in a manner similar to that which occurs when the air number is changed to extremely lean mixtures. This effect is also due to displaced combustion events. Thus, the same control variables may be used for regulating the exhaust gas recycle rate and the ignition timing $\alpha_z$. The circuitry to be described below for changing and adjusting the fuel-air mixture may also be used for adjusting these parameters. The ion currents may also be used for monitoring the engine operation, for measuring the air number as well as for test stands if suitable electronic controllers and processors are employed.

Instead of using the values illustrated by the curves I and S in FIG. 1, which are values integrated over an operational cycle of the engine, it is also possible to use the maximum value of each of these parameters for use as a control variable.

Figure 3:
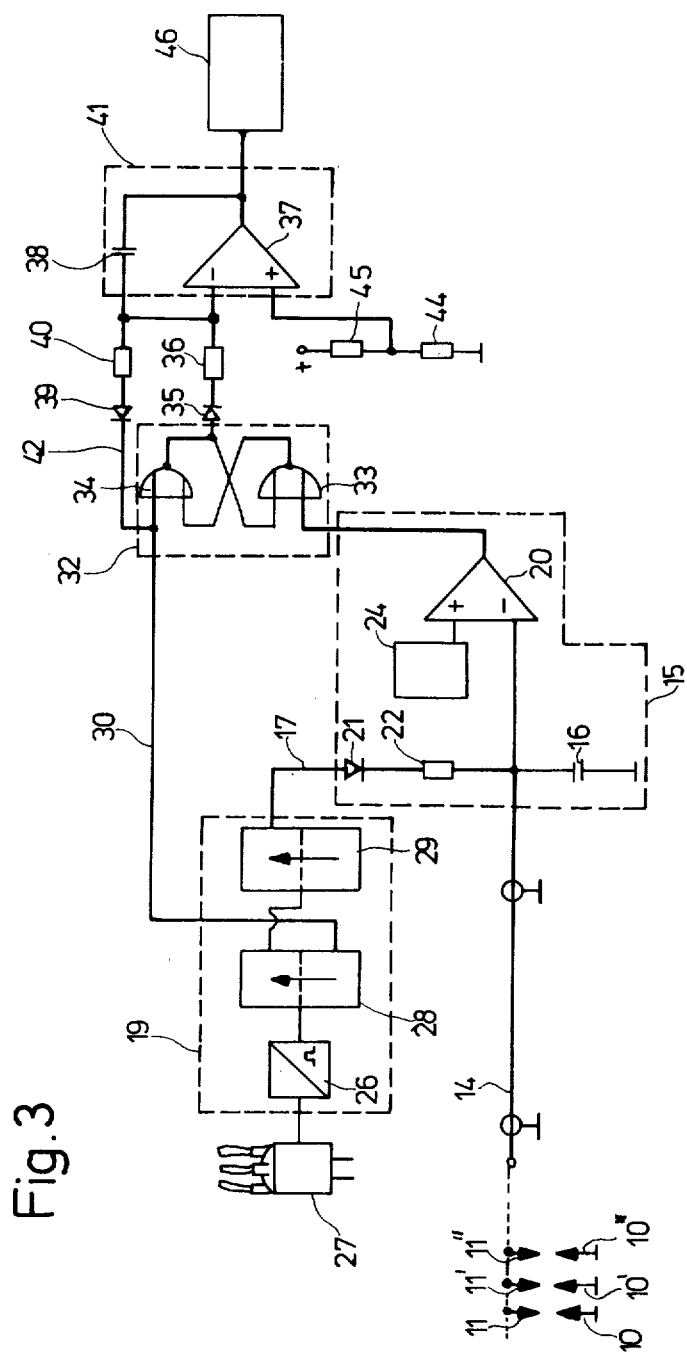
FIG. 3 is a schematic diagram of a first exemplary embodiment of a processor circuit.

FIG. 3 is a schematic diagram of an electronic processor circuit for receiving the currents from the ion current sensor and using them to control the fuel-air mixture of an engine. In this first exemplary embodiment, each cylinder outlet has associated with it a sensor with electrodes 11, 11', 11'', which are joined together. Opposite these electrodes are the ground electrodes 10, 10', 10'' which could also be parts of the exhaust gas tubing. A well-insulated and shielded line 14 leads from the electrodes of the sensors to a comparator circuit 15. The comparator circuit 15 includes a grounded capacitor 16 whose other side is connected to the line 14, a connection line 17 leading to a control circuit 19 and the inverting input of a comparator 20.

The capacitor may be periodically charged over the connection line 17. For this purpose, the connection line 17 includes a diode 21 and a limiting resistor 22. The other input of the comparator is connected to a reference value indicator 24 which delivers to that input of the comparator a constant or variable voltage acting as a command value. The command value may be changed in dependence on other operational parameters, for example the rpm and the throttle valve position of the carburetor.

The circuit 19 which determines the degree of charging of the capacitor includes a pulse-shaping circuit 26 which receives rpm-dependent pulses from an ignition element of the engine, for example the distributor 27. The rpm-dependent pulses are converted into rectangular pulses at rpm-dependent frequency. These pulses are fed to a first monostable flip-flop 28 one of the outputs of which is connected to the input of a second monostable multivibrator 29 and the complementary output of the flip-flop 28 which signals the quiescent state of the flip-flop 28 is connected through a line 30 with a bistable flip-flop 32. The output of the flip-flop 29 related to its flipped-over state is coupled to a connection line 17.

The output of the comparator 20 is connected to the set input of the bistable flip-flop 32. The circuit 32 includes in known manner two NOR gates 33 and 34, the input of the gate 34 beinng connected to the line 30 and the output being connected through a diode 35 and a resistor 36 whith the inverting input of an operational amplifier 37. The output of the operational amplifier 37 is coupled back to its inverting input by a capacitor 38 which thereby imparts to the amplifier an integral behavior. The diode 35 is connected so as to permit positive current to flow to the operational amplifier. A diode 39 is connected in the opposite direction in series with a resistor 40 between the inverting input of the operational amplifier 37 and the line 30 via a wire 42.

The other input of the operational amplifier 37 is connected to a voltage divider consisting of series resistors 44 and 45 to which battery potential is applied. The output of the integral controller 41 formed by the operational amplifier 37 and the integrating capacitor 38 is coupled, for example, with a control element 46 belonging to the metering mechanism of the fuel mixture of the engine. A setting mechanism of this type influences the metering of fuel in known manner by means of a carburetor or by fuel injection nozzles or it controls the amount of bypass air added to a fuel-air mixture. In the same manner, the setting element 46 may affect the quantity of recycled gases for the purpose of exhaust gas detoxication or it may adjust an element of the timing mechanism. The system operates in the following manner. The pulse train of rpm-dependent frequency produced in the pulse former 26 produces output pulses of the same frequency from the first monostable flip-flop 28 having a well-defined pulse width whereas the output of the second monostable flip-flop 29 produces pulses which are displaced in phase with respect to those from the first flip-flop 28 by one pulse width. These pulses, which alternate in amplitude between zero and the battery potential and which are of defined width, serve to charge the capacitor 16 periodically through the diode 21. In the time between the pulses, the capacitor may discharge in accordance with the magnitude of the prevailing ion current through electrodes 11, 11', 11'''. The diode 21 prevents a discharge through the line 17 while a discharge through the input of the comparator 20 is prevented by the high input impedance. When the potential across the capacitor drops below a predetermined threshold which is defined by the command value provided by the command value generator 24, the comparator 20 switches over and produces a signal corresponding to a logical 1 at the set input of the bistable flip-flop 32, i.e., at the NOR gate 33. The complementary output of the first flip-flop 28 then transmits through the line 30 pulses changing from logical 1 to logical 0 to the reset input of the bistable flip-flop 32, i.e., at the NOR gate 34. During the extent of these pulses but only when the set input has a logical 1, may the flip-flop be switched back so that, during the time that the comparator 20 produces a logical 1, the output of the NOR gate 34 again exhibits a logical 1. However, the 1-signal at the output of the comparator 20 returns to 0 at the instant when the capacitor 16 has been fully charged through the connection line 17.

Inasmuch as the non-inverting input of the operational amplifier 37 lies at some voltage in between the full battery voltage and 0, i.e., between the logical 1 and 0, no return current flows through the return line as long as the line 30 experiences the logical 1-signal from the complementary output of the first flip-flop 28. However, once the line 30 experiences the logical 0-signal, a current does flow there whose magnitude is defined by the value of the resistor 40. These conditions prevail in each case for the duration of the flip-over process of the first monostable flip-flop 28. If during that time and because of a missing 1-signal from the comparator 20, the output of the bistable flip-flop 32 has the value 0, then a current flows out of the operational amplifier 37 through the return line 42 to the line 30. If on the other hand the bistable flip-flop 32 exhibits a logical 1, the current flowing through the resistor 36 is determined by the value of that resistor 36 and that current later branches off in one partial current flowing through the return line 42 and another partial current flowing into the operational amplifier 37. For this purpose, the resistor 36 has a smaller value than the resistor 40. The switching circuit just described provides that the integral controller 41 integrates in one or the other directions dictated by the signal from the comparator 20. The output voltage at the operational amplifier 37 is linear because of the feedback through the integrating capacitor 38 from the output of the operational amplifier 37 back to its inverting input. The slope in a particular integrator will be determined by the magnitude of the corresponding resistors 40 and 36. The unsymmetric disposition of the integral controller 41 produces average operational points which cause a shift to larger or smaller values of $\lambda$ than would correspond to the particular value of $\lambda$ during the ion current increase.

Figure 4:
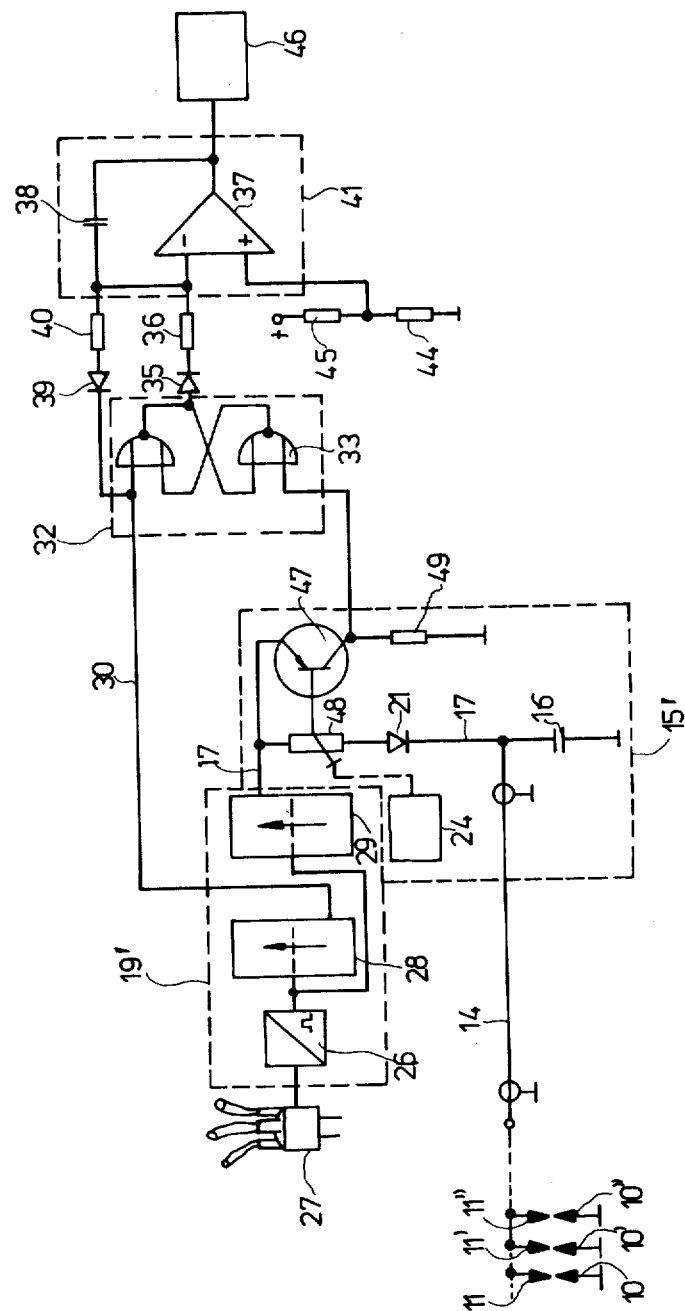
FIG. 4 is a schematic diagram of a second exemplary embodiment of a processor circuit having a relatively low sensor supply voltage.

In other words, the above-described installation uses the ion current corresponding to a particular operational state of the engine and transforms it into a corresponding voltage at a capacitor whose magnitude is between two well-defined potentials and whose remaining voltage is then compared in a comparator 20. The capacitor also serves at the same time as an interference suppressor against voltages which are produced for example in the high-impedance, shielded line 14 through induction. Any voltage peaks occurring there would otherwise cause a rapid switching of the comparator and would prevent a precise control process. The processor circuit illustrated in FIG. 4 is substantially similar to that of FIG. 3. Except for the comparator 15', the system of FIG. 4 is substantially identical to that in FIG. 3 so that these parts are to be taken from the previous description. In contrast to the exemplary embodiment of FIG. 3, the present embodiment dispenses with a comparator 20 which must have a very high input impedance so as not to falsify the relatively weak ion currents occurring when battery voltage is used as the driving potential for the ion currents. In its place, there is provided a transistor 47 and a continuously settable voltage divider 48 within the connection line 17. The tap of the voltage divider 48 is connected to the base of the transistor 47 and may be adjusted by the command value generator 24. Thus, the command value generator may adjust the voltage applied to the base of the transistor in dependence of any other parameter. The emitter of the transistor 47 is supplied with battery voltage through a connection to the line 17 between the control circuit 19 and the voltage divider 48. A collector resistor 49 is connected between the collector of the transistor 47 and ground. The signal is taken off between the collector and the collector resistor and is fed to the set input of the bistable flip-flop 32, i.e., to the input of the NOR gate 33.

In this exemplary embodiment, which is suitable for a PNP transistor, it is the recharging current of the transistor that is used as a measure of the ion current which had passed through the sensors instead, as previously, the voltage occurring during the discharging process. Depending on the degree of discharge of the capacitor in the time elapsing between the recharging pulses provided by the control circuit 19, a charging current of varying magnitude flows through the voltage divider during the charging process. The voltage drop changes accordingly, and so does the voltage taken off at the tap of the voltage divider 48. When the switching voltage of the transistor is exceeded, the transistor switches on and the collector exhibits battery voltage which is then fed to the bistable flip-flop 32 as a logical 1. In contrast to the exemplary embodiment of FIG. 3, the first and second monostable flip-flops 28 and 29 are controlled in synchronism by the pulse shaper 26 so that there is no phase shift in the pulses they produce. However, as in the exemplary embodiment of FIG. 3, the duration of the switch, i.e., the pulse width of the second flip-flop 29 is shorter than that of the first. Furthermore, as before, the bistable flip-flop 32 switches over only when the complementary output of the first flip-flop has a 0-signal and when the collector of transistor 47 has a logical 1.

This exemplary embodiment brings the advantage that a transistor may be used instead of a high impedance comparator. Furthermore, the charging current is substantially easier to define than the capacitor voltage.

Figure 5:
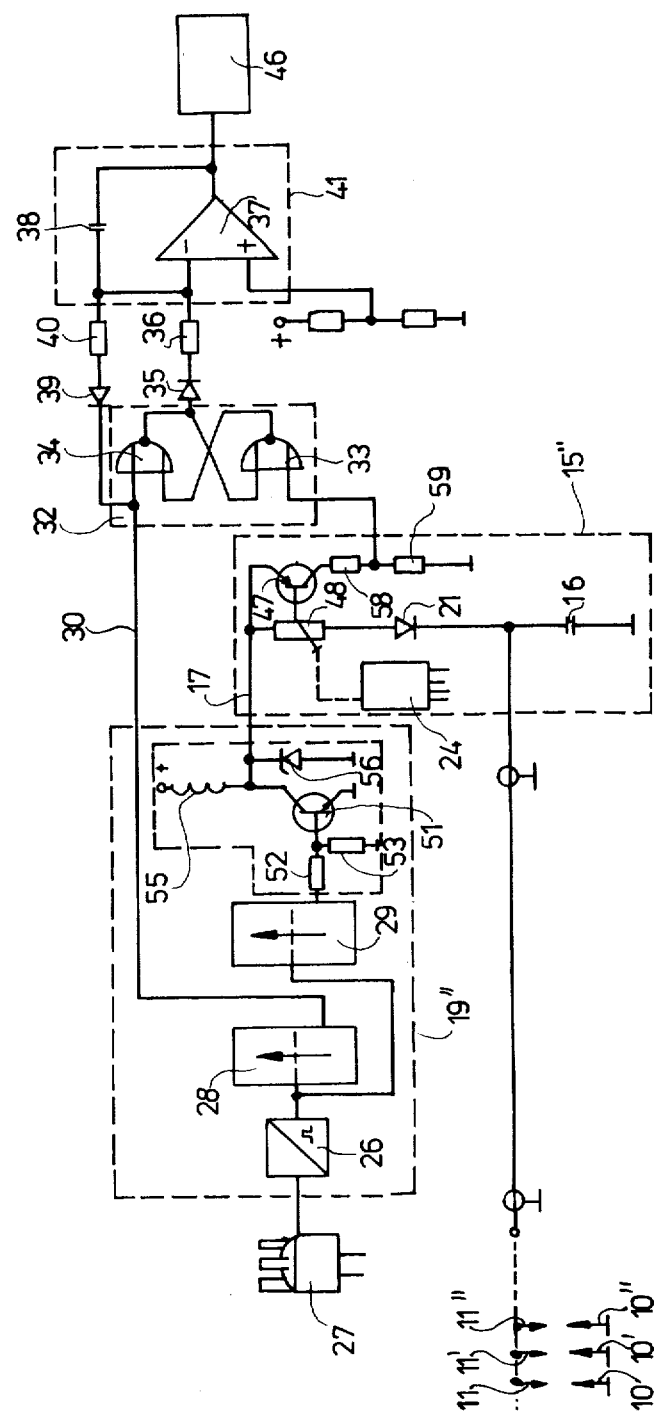
FIG. 5 is a schematic diagram of a third exemplary embodiment of a processor circuit with a high sensor supply voltage.

A variant of the exemplary embodiment of FIG. 4 is illustrated in FIG. 5. This example is substantially similar to the above-described examples but includes additional circuitry for supplying a higher than battery voltage to the capacitor 16 and the electrodes 11, 11', 11". For this purpose, the control circuit 19" is modified so as to place between the complementary output of the flip-flop 29 and the line 17 a circuit including a transistor 51 whose base is connected to the complementary output of the monostable flip-flop 29 via a voltage divider consisting of two resistors 52 and 53. The collector of the transistor 51 is connected to the positive battery voltage and its emitter is grounded. The collector resistor is a coil 55 of high inductivity and the connecting line 17 is connected between the junction of the coil 55 and the collector of the transistor 51 leading to the capacitor 16. A Zener diode 56 is connected in parallel with the transistor 51 between the line 17 and ground preventing current flow to ground.

The circuit just described operates substantially in the same manner as that of FIG. 4. Thus, the monostable flip-flops 28 and 29 are simultaneously flipped over by the pulse from the pulse shaping stage and thus both generate a pulse of well-defined width at rpm-dependent frequency. The time constant of the second flip-flop 29 is also shorter than that of the first flip-flop 28. As long as the complementary output of the second flip-flop 29 carries a voltage, the transistor 51 conducts and a constant current flows through the coil 55. The connection line 17 is at 0 potential thus the transistor 47 remains blocked. When the second flip-flop 29 switches over, the base of the transistor 51 goes to 0 and blocks this transistor. This interruption produces an inverse inductive potential which is limited in magnitude by the Zener diode 56. During this time, the connecting line 17 carries a high positive voltage which causes the capacitor 16 to be recharged. At the same time, as already described with respect to the previous example, the transistor 47 is switched on. Thus, the input of the NOR gate 33 in the bistable flip-flop 32 receives a voltage serving as a logical 1 whose magnitude is defined by the voltage divider connected between the ground and the collector of the transistor 47 and consisting of the resistors 58 and 59. This signal causes the bistable flip-flop 32 to be swtiched over if a pulse is present at the line 30.

The just described exemplary embodiment brings the advantage that a substantially greater measuring potential may be used which results in a higher sensitivity of the whole system. Furthermore, the use of a transistor 47 in place of a comparator makes this installation economically more favorable and less subject to interference.

Figure 6:
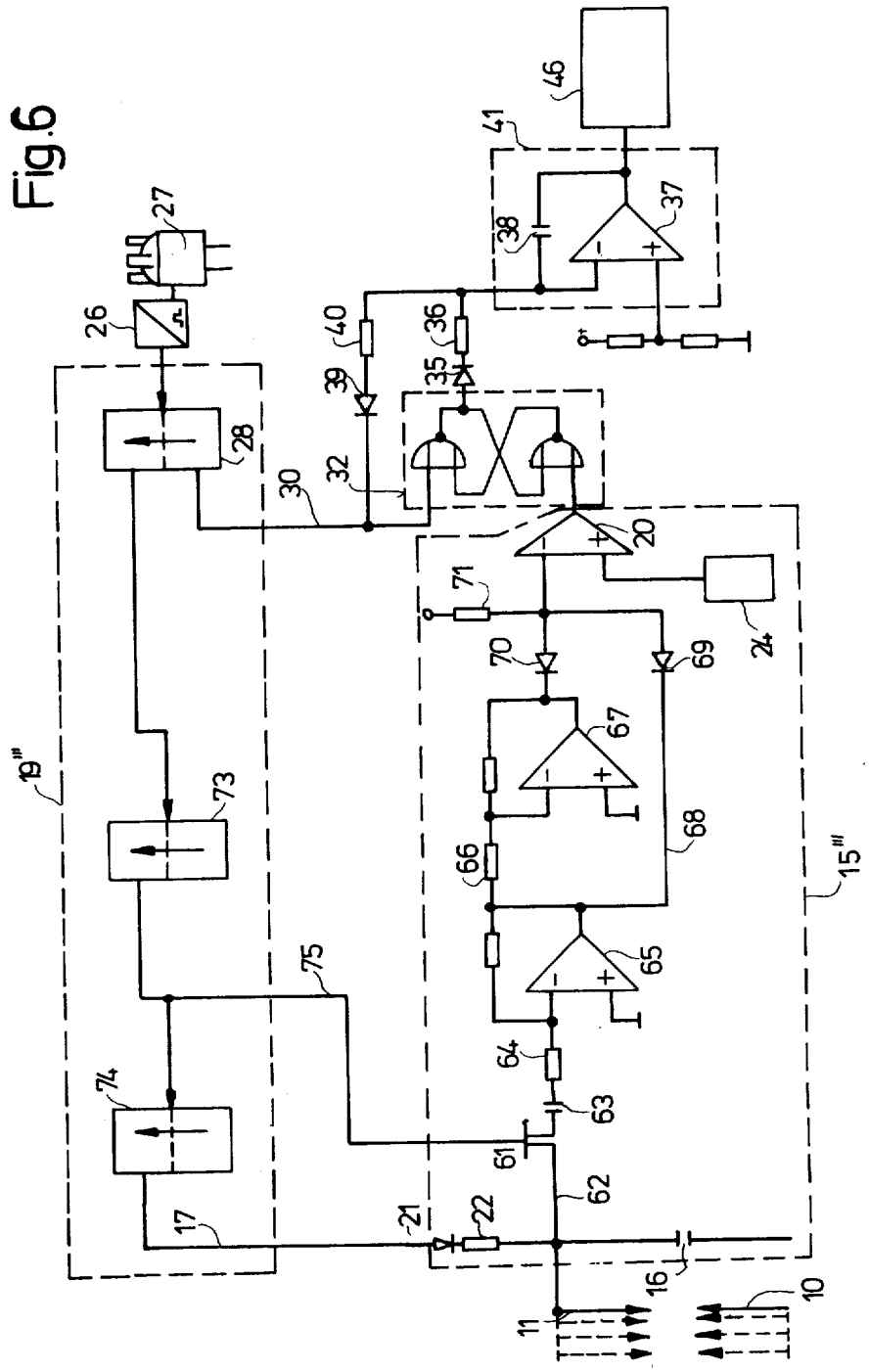
FIG. 6 is a schematic diagram of a fourth exemplary embodiment of a processor circuit which uses the changes of the integrated ion currents in several sequential cycles in the cylinder.

The exemplary embodiment illustrated in FIG. 6 is a variant of the circuit of FIG. 3. The output stage is built in the same way as that of the example of FIG. 3 so that any information concerning the comparator 20, the bistable flip-flop 32 and the integral controller 41 may be had from the description of FIG. 3. Identical elements carry the same reference numerals. In deviation from the exemplary embodiment of FIG. 3, the present variant has a switch 61 in the connecting line 62 which connects the line 17 with a comparator 20. Following the switch 61 is a capacitor 63 which is connected through a resistor 64 with the inverting input of an operational amplifier 65. The output of that amplifier in turn is connected to an adapting resistor 66 at the inverting input of a second operational amplifier 67. Finally, a line 68 leads from the output of the first operational amplifier 65 via a diode 69 to the output of the second operational amplifier 67. A further diode 70 is inserted in parallel to the diode 69 between the output of the second operational amplifier 67 and the junction with the line 68. Behind the junction with the line 68, the output of the second operational amplifier 67 is connected to the inverting input of the comparator 20. The inverting input is connected to the positive potential via a resistor 71. The non-inverting input of the comparator 20 is connected with a command value generator 24, just as in the example of FIG. 3, by means of which the threshold of the comparator can be adjusted. The diodes 69 and 70 are both connected to prevent positive current flow to the comparator 20.

In this example, the switch 61 is a field effect transistor which is periodically closed by the control circuit 19''' in advance, by one phase, of the charging process of the capacitor 16.

The control circuit 19''' includes three sequential monostable flip-flops, the first of which is supplied with rectangular pulses of rpm-dependent frequency by the pulse shaper 26. The output of the first flip-flop 28 is connected to the input of a second flip-flop 73 whose output, in turn, is connected to a third monostable flip-flop 74. The complementary output of the first flip-flop 28 branches off to a clock line 30 leading to the bistable flip-flop 32. The output of the second monostable flip-flop 73 controls the switch 61 through a line 75 and the connecting line 17 branches off from the output of the third monostable flip-flop to the capacitor 16 and includes the diode 21 and the resistor 22, as was the case previously.

The just described circuit operates as follows. The control circuit 19''' produces at its output pulses of defined width and rpm-dependent frequency and these pulses are phase shifted by one pulse width. This means that the capacitor 16 can be charged through the connecting line 17 only if the switch 61 has previously been opened. During this opening time, the capacitor 16 is connected in parallel to the capacitor 63 which is grounded through the first operational amplifier 65 and its non-inverting input. Depending on the magnitude of the differential charge, an equalizing current flows between the two capacitors in the direction of the prevailing potential difference. Accordingly, the output of the first operational amplifier 65 also carries a voltage which, depending on the direction of the equalizing current, is carried either through the line 68 and the diode 69 or through the second operational amplifier 67 which inverts it and through the diode 70 to the inverting input of the comparator 20. Depending on whether this voltage pulse exceeds the set command value at the comparator, this comparator delivers a 1 or a 0 to the bistable flip-flop 32 which processes it in the same manner as previously described, for example with respect to FIG. 5. When the switch 61 is closed, the phase-shifted pulse from the third monostable flip-flop recharges the capacitor whereas the previous value is stored in the capacitor 63. Depending on the degree of ionization of the exhaust gases, a smaller or larger discharge current flows through the ion current sensors during the time until the switch 61 is opened. When the switch 61 is opened, the potenial on the capacitor 16 may be higher, equal to or smaller than that on the capacitor 63. The difference of this voltage between the previous and the subsequent cycle of the engine is expressed in the amount and direction of the equalizing current. Actually, use is made only of the magnitude of the equalizing current and, when a predetermined magnitude is exceeded, the integral controller alters the action of the fuel metering system in the direction of a rich mixture. It is this circuit according to FIG. 6 which processes the data in curve S in the diagram of FIG. 1 for regulating the fuel mixture fed to the engine. It will be seen that very lean operational states of the engine are thus subject to control. In comparison to the regulation of the ion current, the present system provides the advantage that the fluctuations begin to increase in the neighborhood of the air number $\lambda = 1$. This system can also be used very advantageously for controlling the exhaust gas recycle rate and the ignition timing angle. Other possibilities for control are given, as in previously described examples, by changing the command value generator in dependence on engine variables such as rpm, induction tube pressure or throttles valve angle, as well as cooling water temperature.

The above-described method and apparatus thus provides manifold possibilities for controlling the operation of an engine and for diagnosing the composition of the exhaust gases in such an engine. In its operation, the apparatus uses a cheap sensor not subject to interference and a relatively simple control system.

The foregoing relates to preferred exemplary embodiments of the invention, it being understood that other embodiments and variants thereof are possible within the spirit and scope of the invention, the latter being defined by the appended claims.

What is claimed is:

1. A method for controlling the fuel-air mixture of an internal combustion engine, said engine including combustion chambers, inlet conduits leading to said combustion chambers and exhaust conduits leading from said combustion chambers to the atmosphere, comprising the steps of placing an ion-current sensor in the exhaust conduit for measuring an ion-current;

generating a nominal value of the ion-current;

comparing the magnitude of the ion-current with the nominal value and generating a signal representing the difference between the measured value of the ion-current and said nominal value; and periodically integrating a signal derived from the signal representing the difference between the measured value of the ion-current and said nominal value, especially during one working cycle of a piston of the engine, and altering the fuel-air mixture of the engine in dependence on the result of the integration.

2. A method as defined in claim 1, wherein said ion-current sensor is placed in the immediate vicinity of the exhaust valves of the engine.

3. A method as defined by claim 1, wherein the result of integration is used to change the ignition timing of the engine.

4. A method as defined by claim 1, wherein the generated nominal value is changed in dependence on other operational parameters of the engine.

5. A method as defined by claim 1, wherein the step of comparing uses the increasing ion-currents resulting from the integration in the region of the air number $\lambda \leq 1$ as a controlled variable.

6. A method as defined by claim 5, wherein the control variable is the increase of the integrated ion-currents at air numbers $\lambda \leq 1$ and $\lambda > 1$ and wherein the transition between these two operational domains is effected by a pre-control of the air number.

7. A method as defined by claim 1, including the further step of comparing the results of said integration with one another.

8. A method as defined by claim 1, wherein the step of comparing includes comparing the fluctuations of sequential values of said integration with respect to the instantaneous value $I/|I|$.

9. An apparatus for controlling the fuel-air mixture of an internal combustion engine, said engine including at least one combustion chamber, inlet conduit means leading to said combustion chamber, exhaust conduit means leading from said at least one combustion chamber to the atmosphere, and fuel mixture preparation means, said apparatus comprising:

at least one ion-current sensor, disposed within said exhaust conduit means for measuring the amount of ionized exhaust gas and for generating a sensor signal indicative thereof;

means for generating a nominal value;

a comparator connected to said at least one ion-current sensor and to said means for generating a nominal value for comparing said sensor signal with the nominal value for generating a signal representing the difference between the measured value of the ion-current and said nominal value;

an integral controller, commanded by said comparator, to periodically integrate a signal derived from the signal representing the difference between the measured value of the ion-current and said nominal value, especially during one working cycle of a piston of the engine, and a final control element, controlled by said integral controller, for adjusting said fuel-mixture preparation means as a function of the results of integration.

10. An apparatus as defined by claim 9, wherein said integral controller includes an operational amplifier having an integrating capacitor connected between its output and its inverting input and wherein there is disposed behind the integral controller a bistable flip-flop whose reset input is connected with a control circuit by means of which the bistable multivibrator is periodically called upon to process the output signal of the comparator.

11. An apparatus as defined by claim 10, wherein the inverting input of said operational amplifier is connected through a first resistor and a diode to the control circuit and via a second resistor and an oppositely connected diode with the output of said bistable multivibrator, the second resistor being of a smaller value than said first resistor.

12. An apparatus as defined by claim 9, wherein said comparator uses the ion-current as control variable by testing the remanent voltage or the charging current of a periodically chargeable second capacitor.

13. An apparatus as defined by claim 12, wherein said comparator includes said second capacitor one of the electrodes of which is connected to ground whereas the other electrode is connected to at least one of said ion-current sensors the other electrode also being connected with a threshold switch as well as with said control circuit via a line containing a diode; whereby said capacitor may be charged by pulses of preferably rpm-dependent frequency.

14. An apparatus as defined by claim 13, wherein the operating voltage of the ion-current sensor is the battery voltage of a motor vehicle.

15. An apparatus as defined by claim 13, wherein said threshold switch includes a comparator element connected with a nominal value generator.

16. An apparatus as defined by claim 13, wherein said threshold switch includes a transistor the collector emitter path of which is connected in parallel with said second capacitor and the base of which is connected to an adjustable voltage divider for receiving the charging current through said second capacitor and acting as the threshold generator, the collector resistor of said transistor being connected with said integral controller.

17. An apparatus as defined by claim 13, wherein said threshold switch includes a comparator element connected with a threshold indicator and wherein the connecting line between said second capacitor and said comparator element includes a switch which is activated by said control circuit by a pulse which is advanced by one phase with respect to the charging pulse for said second capacitor and wherein the circuit further includes a differentiator and a rectifier subsequent to said switch.

18. An apparatus as defined by claim 17, wherein said differentiator includes an operational amplifier the inverting input of which is connected with said switch via a resistor and a third capacitor.

19. An apparatus as defined by claim 17, wherein said rectifier includes a further operational amplifier the output of which is connected to a diode and a further parallel diode connected between the inverting input and the output of said further operational amplifier.

20. An apparatus as defined by claim 13, wherein said threshold switch further includes a comparator element connected with a nominal value generator and wherein said control circuit includes a pulse shaping circuit connected with the ignition system of the engine, said pulse shaping circuit controlling a first monostable flip-flop behind which is connected a phase shifting second monostable flip-flop the output of which is connected to said second capacitor and wherein the complementary output of said first monostable flip-flop is connected to the reset input of said bistable flip-flop.

21. An apparatus as defined by claim 13, wherein said threshold switch further includes a comparator element connected with a nominal value generator and wherein said control circuit includes a pulse shaping circuit coupled to the ignition system of the engine, said pulse shaping circuit controlling a first and a second monostable multivibrator, wherein the output of said second monostable multivibrator is connected to said second capacitor and wherein the complementary output of said first monostable multivibrator is connected with the reset input of said bistable flip-flop.

22. An apparatus as defined by claim 21, wherein the complementary output of the quiescent position of said second monostable multivibrator is connected via a voltage divider with the base of a transistor having an inductive coil as collector impedance, the collector of which is connected via a Zener diode to ground and is also connected to said comparator.

23. An apparatus as defined by claim 13, wherein said threshold switch includes a comparator element and a nominal value sensor and wherein the connection between said second capacitor and said comparator element includes a switch which is actuated by said control circuit and where there is connected beyond said switch a differentiator and a rectifier, and wherein said control circuit includes a pulse shaping circuit connected to the ignition system of the engine, said pulse shaping circuit actuating a first monostable multivibrator and, in sequence, a second monostable multivibrator for the generation of mutually phase shifted pulses and, behind that, a third monostable multivibrator, the complementary output of said first multivibrator being connected to the reset input of said bistable multivibrator and the output of said second monostable multivibrator being connected to said switch, while the output of said third monostable multivibrator is connected to said second capacitor.

24. An apparatus as defined by claim 9, wherein said ion-current sensor is a spark plug.

* * * * *